United States Patent [19]

Fuger et al.

[11] 4,133,813

[45] Jan. 9, 1979

[54] CYCLIC NITRILE CARBONATE-CONTAINING COMPOUNDS

[75] Inventors: Karl E. Fuger, Ettingen, Switzerland; Ming N. Sheng, Cherry Hill, N.J.

[73] Assignee: Atlantic Richfield Company, Los Angeles, Calif.

[21] Appl. No.: 730,058

[22] Filed: Oct. 6, 1976

Related U.S. Application Data

[63] Continuation-in-part of Ser. No. 696,994, Jun. 17, 1976, abandoned, which is a continuation of Ser. No. 595,249, Jun. 17, 1975, abandoned.

[51] Int. Cl.$^2$ .......................................... C07D 273/00
[52] U.S. Cl. .......................... 260/307 A; 260/307 C; 521/149; 526/260
[58] Field of Search ..................................... 260/307 A

[56] References Cited

U.S. PATENT DOCUMENTS 3,946,014  3/1976  Fuger et al. ..................... 260/307 A

*Primary Examiner*—Donald G. Daus
*Assistant Examiner*—David E. Wheeler
*Attorney, Agent, or Firm*—Coleman R. Reap

[57] ABSTRACT

Cyclic nitrile carbonate-containing compounds having the structural formula:

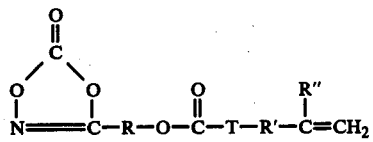

wherein T is O, S, or NR'''; R and R' are organic radicals; R'' is hydrogen, halogen or an organic radical and R''' is hydrogen or an organic radical are prepared by reacting a cyclic nitrile carbonate-containing chloroformate having the structural formula:

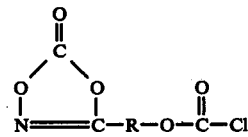

with a nucleophilic compound having the structural formula:

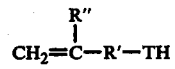

wherein T, R, R', R'' and R''' are as defined above, under conditions such that the TH group will react with the chloroformate group, but no reaction will occur involving either the cyclic nitrile carbonate group or the

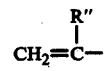

group. The novel compounds of the invention are useful in the preparation of crosslinkable polymers.

22 Claims, No Drawings

CYCLIC NITRILE CARBONATE-CONTAINING COMPOUNDS

RELATED APPLICATIONS

This application is a continuation-in-part of application Ser. No. 696,994 filed June 17, 1976 which, in turn, is a continuation of application Ser. No. 595,249 filed June 17, 1975.

BACKGROUND OF THE INVENTION

The present invention relates to novel chemical compounds and their synthesis. More particularly, it is concerned with the preparation of ethylenically unsaturated cyclic nitrile carbonate group-containing compounds which undergo addition-type polymerization.

The recent boom in industrial and home construction has created an increased demand for engineering materials. This demand has not been satisfactorily met by producers of steel and other conventional building and construction materials. Furthermore, because of the widely varying needs in specialty fields, there is a continuous demand for a wide range of construction materials having different physical properties. These needs have been frequently satisfied by the use of polymeric materials, which can be formulated to have various physical properties. Due to the successful use of polymers in industry, there is continuous research for new monomers from which useful polymers can be produced. Monomers which are of particular interest are those which readily polymerize to polymers which can be easily crosslinked to produce rigid plastics having good physical strength properties and resistance to chemical attack.

PRIOR ART

In U.S. Pat. No. 3,609,163 herein incorporated by reference, are disclosed, inter alia, certain cyclic nitrile carbonate group-containing chloroformates of the general formula:

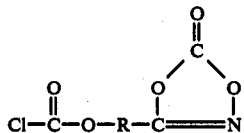

wherein R is a hydrocarbon. These chloroformates are disclosed in the above-mentioned U.S. Patent as being useful as blowing agents for vinyl resins and the like and, as regards certain of the chloroformates, as being useful as precursors for ethylenically-unsaturated cyclic nitrile carbonate compounds.

SUMMARY OF THE INVENTION

It has now been found that useful addition polymerizable cyclic nitrile carbonate group-containing monomers can be prepared from chloroformates having the above structural formula wherein R is a difunctional organic radical.

Accordingly, it is an object of the invention to present new monomers from which useful addition-type polymers can be prepared. It is another object of the invention to present new addition polymerizable monomers which contain functional groups which are useful for crosslinking polymers produced from these monomers. It is another object of the invention to present new polymer-producing compounds containing both ethylenic unsaturation and cyclic nitrile carbonate groups. It is another object of the invention to present a new method for preparing polymer-producing compounds. These and other objects of the invention will become manifest to those skilled in the field upon perusal of the following description and examples.

The novel compounds presented in this invention have the structural formula:

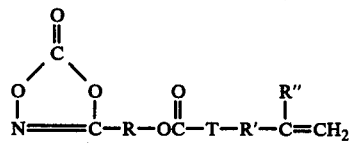

wherein T is O, S or NR''', R and R' are divalent organic radicals free of groups that are reactive with cyclic nitrile carbonate groups of chloroformate groups, R contains 1 to 20 carbon atoms and R' contains 1 to 50 carbon atoms; R'' is hydrogen, halogen or a monovalent hydrocarbon containing 1 to 8 carbon atoms; and R''' is hydrogen or a monovalent hydrocarbon radical containing 1 to 8 carbon atoms. The above compounds are prepared by reacting a cyclic nitrile carbonate group-containing chloroformate with a nucleophilic compound containing a terminal, ethylenically unsaturated group. The reaction is carried out at a temperature below that at which the cyclic nitrile carbonate group reacts with the nucleophilic compound and below the decomposition temperature of the cyclic nitrile carbonate group.

DESCRIPTION OF THE INVENTION

The cyclic nitrile carbonate-containing chloroformates useful in the preparation of the novel compounds of the invention have the structural formula:

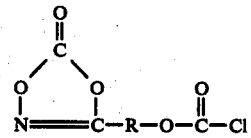

wherein R is a divalent, essentially hydrocarbonaceous organic radical having 1 to 20 carbon atoms. The term "essentially hydrocarbonaceous" is used in this specification to describe organic radicals which are comprised of carbon and hydrogen as essential components but which may contain elements other than carbon and hydrogen, particularly oxygen, nitrogen, sulfur, or the halogens, either in pendent moieties or in a main chain, provided such other elements do not change the main characteristic intended for the organic radicals, that is, that they be free of groups or elemental atoms that would be reactive with the cyclic nitrile carbonate groups or the chloroformate groups present in the reactants or novel products of the invention, such as reactive hydrogen-containing groups as determined by the Zerewitinoff test, or which would interfere with the desired polymerization reaction of the terminal ethylenically unsaturated group. A compound which contains reactive hydrogen as determined by the Zerewitinoff test is one which, when contacted with a Grignard solution of methyl iodide, will effect the liberation of methane by the decomposition of the Grignard reagent. Chloroformate compounds from which the compounds of the invention may be prepared can contain, in addition to carbon and hydrogen atoms, pendent halogen atoms, such as chlorine or bromine atoms; oxygen-containing groups, such as ester, ether or ketone groups; sulfur-containing groups, such as thioester, thioether or thione groups; nitrogen-containing, such as nitro, tertiary amine, or nitrile groups; or groups containing mixtures of the above-mentioned atoms such as amide, urea or thiourea groups. R is usually comprised predominantly of carbon and hydrogen atoms.

R may be aromatic and have, e.g., 1 to 3 rings (fused or non-fused) or nonaromatic and, when nonaromatic, can be cyclic or acyclic and saturated or ethylenically unsaturated. The cyclic nitrile carbonate group may be attached to an aromatic ring carbon atom, a cycloaliphatic ring atom or a non-ring carbon atom. R can be straight chain only or it can contain branch chains. R preferably contains 3 to 12 carbon atoms and in the most preferred embodiment R is a saturated hydrocarbon radical and contains 3 to 6 carbon atoms.

One method for preparing the chloroformate starting material used in the reaction of the present invention is disclosed in the aforementioned U.S. Pat. No. 3,609,163. Briefly, the chloroformates can be prepared by phosgenating a hydroxyl group-containing monohydroxamic acid, for example as represented in the following equation:

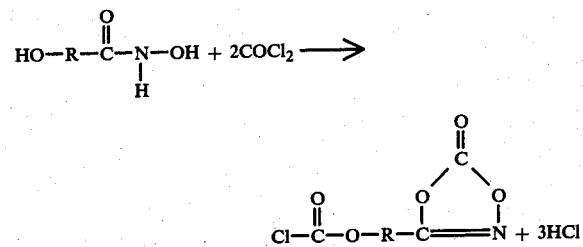

The hydroxyl group-containing hydroxamic acid can, in turn, be prepared by reacting a lactone with hydroxylamine, as represented in the following equation:

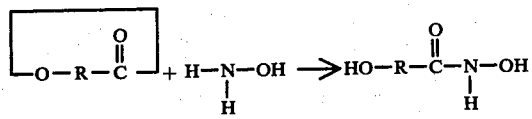

The above-discussed method of preparing the chloroformates is generally preferred for preparing chloroformates in which the R group is unbranched rather than branched, and saturated rather than unsaturated. Accordingly, the chloroformate used in the present invention will most often be so composed when prepared by the above process; also, its R group will frequently contain from 3 to 5 carbon atoms.

Where the chlorocarbonyloxy group of the chloroformate is separated from the cyclic nitrile carbonate group by a paraffinic carbon-to-carbon chain of 2 carbon atoms, then the chloroformate is capable of partially decomposing to yield ethylenically-unsaturated cyclic nitrile carbonate compounds. As discussed in the aforementioned U.S. Pat. No. 3,609,163, the decomposition is catalyzed by organic tertiary amines which have pK values below about 5. As will be hereinafter discussed in greater detail, it can be advantageous to include a basic compound such as a tertiary amine in the condensation reaction mixture of the present invention. Where such is used, then it will be preferred that the chloroformate starting material have at least 3 carbon atoms separating the non-ring oxygen atom from the nitrile carbon atom, the purpose being to avoid the situation wherein an unsaturation-yielding partial decomposition reaction would compete with the desired condensation reaction of the present invention. Most preferably, in fact, the minimum 3 carbon atom separation is employed regardless of whether a basic compound is present in the condensation reaction mixture.

Examples of cyclic nitrile carbonate group-containing chloroformates include saturated aliphatic compounds, such as 5-(chlorocarbonyloxypropyl)-1,3,4-dioxazol-2-one, 5-(chlorocarbonyloxypentyl)-1,3,4-dioxazol-2-one, 5-(chlorocarbonyloxydecyl)-1,3,4-dioxazol-2-one, 5-(chlorocarbonyloxy-3-decylpentyl)-1,3,4-dioxazol-2-one; unsaturated aliphatic compounds, such as 5-(chlorocarbonyloxyhex-2-enyl)-1,3,4-dioxazol-2-one; saturated and unsaturated cycloaliphatic compounds, such as 5-(4-chlorocarbonyloxycyclohexyl)-1,3,4-dioxazol-2-one and 5-(4-chlorocarbonyloxy-2-cyclohexenyl-1,3,4-dioxazol-2-one; aromatic compounds such as 5-(4-chlorocarbonyloxyphenyl)-1,3,4-dioxazol-2-one, 5-(4-chlorocarbonyloxy-2-ethylphenyl)-1,3,4-dioxazol-2-one, 5-[3-(4-chlorocarbonyloxy-2-methylphenyl)-propyl]-1,3,4-dioxazol-2-one, 5-(5-chlorocarbonyl-oxynaphthyl)-1,3,4-dioxazol-2-one, etc.

Examples of suitable chloroformate compounds which contain the above-mentioned oxygen, sulfur and nitrogen-containing groups are 5-(5-hydroxy-3-oxopentyl)-1,3,4-dioxazol-2-one, chloroformate ester; 5-[6-(2-hydroxyethoxy)hexyl]-1,3,4-dioxazol-2-one, chloroformate ester; 5-[3-(hydroxymethylcarbonyloxy)propyl]-1,3,4-dioxazol-2-one, chloroformate ester; 5-(5-hydroxy-3-thioxopentyl)-1,3,4-dioxazol-2-one, chloroformate ester; 5-[6-(2-hydroxyeththio)-1,3,4-dioxazol-2-one, chloroformate ester; 5-[3-(3-hydroxypropylcarbonylthio)propyl]-1,3,4-dioxazol-2-one, chloroformate ester; 5-[6-(2-hydroxyethylmethylamino)hexyl]-1,3,4-dioxazol-2-one, chloroformate ester; 5-[4-(2-hydroxyethyl)-3-nitrophenylmethyl]-1,3,4-dioxazo-2-one, chloroformate ester; 5-(2-cyano-3-hydroxypropyl)-1,3,4-dioxazol-2-one, chloroformate ester; 5-[3-(hydroxyacetamido)propyl]-1,3,4-dioxazol-2-one, chloroformate ester; 5[3-(hydroxymethylureido)propyl]-1,3,4-dioxazol-2-one, chloroformate ester; and 5-[3-(hydroxymethylthioureido)propyl]-1,3,4-dioxazol-2-one, chloroformate ester.

Most preferably, the chloroformate is soluble in one or more of the following solvents: water, chloroform, diethylether, benzene, and p-dioxane. This solubility permits the use of one or more of those solvents in the condensation reaction, which, as hereinafter discussed, is the preferred manner of conducting the reaction. Examples of preferred chloroformates which are soluble in one or more of these solvents are 5-(chlorocarbonyloxypentyl)-1,3,4-dioxazol-2-one, 5-(chlorocarbonyloxybutyl)-1,3,4-dioxazol-2-one, and 5-(chlorocarbonyloxypropyl)-1,3,4-dioxazol-2-one.

The nucleophilic compounds useful in the preparation of the novel compounds of the invention have the structural formula:

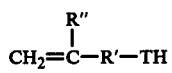

wherein I is O, S, or NR''', R' is carbonyl or a divalent, essentially hydrocarbonaceous organic radical having 1 to 50 carbon atoms, R" is hydrogen, halogen, or a monofunctional essentially hydrocarbonaceous organic radical having 1 to 8 carbon atoms, and R''' is hydrogen or a monofunctional, essentially hydrocarbonaceous organic radical having 1 to 8 carbon atoms. When R', R" and R''' are organic radicals they may contain halogen substituents or any of the oxygen, sulfur or nitrogen groups which R may contain, as described above. As is the case with R, R', R", and R''' are usually comprised predominantly of carbon and hydrogen atoms.

The nucleophilic compound can be aromatic or nonaromatic (i.e., aliphatic or cycloaliphatic) and the nucleophilic groups (i.e., those designated as —TH in the above formula) can be held either by non-aromatic carbon atoms or by aromatic carbon atoms (i.e., attached directly to an aromatic ring). Where the nucleophilic compound is non-aromatic, it can be saturated or ethylenically or acetylenically unsaturated. Where the nucleophilic groups are held by non-aromatic carbon atoms, they (the nucleophilic groups) can be primary, secondary, or tertiary. (To clarify, by a primary nucleophilic group is meant one which is held by a carbon atom which also holds 2 hydrogen atoms.) Where the nucleophilic compound is aromatic, it is often preferred that it contain either 1 or 2 benzene rings; and, if the latter, preferably non-fused rings.

As can be appreciated the nucleophilic compound can be an alcohol, a mercaptan, a primary amine or a secondary amine depending on whether T is O, S or NR'''. When T is NR''' and R''' is hydrogen the nucleophilic compound is terminated with a primary amine an when R''' is a monofunctional, essentially hydrocarbonaceous group the nucleophilic groups it terminated with a secondary amine group. When R''' is essentially hydrocarbonaceous it is preferably a saturated hydrocarbon group having 1 to 8 carbon atoms. R' may contain only hydrogen and carbon atoms in which case the unsaturated portion of the nucleophilic compound will be olefinic or halogen-substituted olefinic. R' may contain hetero atoms such as in-chain oxygen atoms resulting from the reaction of alkylene oxides or epoxides with other functional groups or in-chain nitrogen atoms. R' may also be carbonyl in which case the unsaturated portion of the nucleophilic compound may be an acrylic or substituted acrylic compound or other omega-unsaturated acid. R' may also contain carbonyl, carboxyl-ester or other, and in-chain hetero atoms such as are obtained by the reaction acrylic-type compounds with alkylene oxides or diols in which case the unsaturated portion of the nucleophilic compound will be an unsaturated ester. R' may contain up to 50 carbon atoms but preferably contains up to 30 carbon and most preferably up to 12 carbon atoms and may include a carbonyl carbon atom.

When R" is hydrogen the unsaturated end group may be a mono-olefinic group or an unsubstituted end group such as an unsubstituted acrylic or other such group, etc. When R" is a saturated hydrocarbon the end group may be a hydrocarbon substituted mono-olefinic group such as a branched mono-olefinic group or a hydrocarbon substituted acrylic group, etc. When R" is an unsaturated hydrocarbon the end group may be a diolefinic group, etc. When R" is halogen the unsaturated end group may be a halogen substituted olefinic group, a halogen substituted acrylic group, etc. When R" is a hydrocarbon it contains up to 8 carbon atoms and preferably up to 3 carbon atoms and often contains one ethylenically unsaturated group.

Depending on the nature of R', R" and R''' the nucleophilic compound may contain up to 48 carbon atoms. In preferred embodiments the nucleophilic compound has 3 to 12 carbon atoms.

The nucleophilic compound may also be an epoxy terminated compound having a terminal ethylenically unsaturated group on the other end of the molecule. The epoxy group will react with the chloroformate group to produce the desired compounds.

Exemplary of nucleophilic compounds which may be used in the preparation of the novel compounds of the invention are the following unsaturated acids, esters, alcohols, thiols, and amines. Acrylic acid, α-methyacrylic acid, α-ethacrylic acid, 2-hydroxymethyl acrylate, 2-hydroxypropyl methacrylate, 4-mercaptobutyl ethacrylate, 5-aminopentyl acrylate, α-chloroacrylic acid, 3-hydroxypropyl 2-chloroacrylate, acrylamide, thioacrylic acid, 1 butenoic acid, 2-hydroxyethyl 3-butenoate, 3-mercaptopropyl 4-pentenoate, 2-aminoethyl 3-butenoate, N-propyl-2-aminoethyl acrylate, 2-propen-1-ol, 3-methyl-3 buten-1-ol, 2-hydroxymethyl-1,3-butadiene, 5-chloro-5 hexen-1 ol, 2-allylphenol, 2-propenylamine, 2-allylthiophenol, 3-butenylamine, 3-ethyl-4-pentenylamine, N-butyl-3-butenylamine, 2 allyl-1-aminomethylbenzene, 2-(3-aminopropyl)-1,3-butadiene, 2-chloro-2-propenylamine, 2-propenylurea 2-propene-1thiol 3-butene-2-thiol, 3-(4-mercaptobutyl)-1,3-butadiene, 3-chloro-3-butene-1-thiol.

Exemplary of compounds containing non-interfering oxygen-, sulfur- and nitrogen-containing groups are 5-hydroxy-1-penten-3-one; 4 mercaptomethyl-4pentene-2-thione; 1-ethyl-3-[2-(5-hexenylamino)ethyl]urea; 3-(2-propenylamino)propionamide; 3-(p-nitrobenzyl)-3-buten-1-ol; 3-(3-butenylamino)propionitrile; and 1-(2-aminoethyl)-3-(2-propenyl)-2-thiourea.

Higher molecular weight nucleophilic compounds such as those derived from the reaction of acids or alcohols with high molecular organic compounds are also contemplated as useful in preparing compounds of the invention. Representative higher molecular weight compounds are the reaction products of unsaturated acids or alcohols, amines or thiols with alkylene oxides, such as ethylene oxide and propylene oxide. As stated above, these nucleophilic compounds may contain up to 48 carbon atoms. Examples of such compounds are the acrylic acid ester of polyethylene oxide, the thiomethacrylic acid ester of polypropylene oxide, the reaction product of acrylamide and polyethylene oxide, the 2-propenol ether of polyethylene oxide, the 3-butenethiol ether of polyethylene oxide and the reaction product of 2-propenylamine and polyethylene oxide. Epoxy compounds which may serve as the nucleophilic compound include 4,5-epoxy-1-pentene, etc.

As with the chloroformate, it is preferred that the nucleophilic reactant be soluble in one or more of the following solvents: water, chloroform, diethyl ether, benzene, and p-dioxane.

The novel compounds of the invention are prepared by reacting the cyclic nitrile carbonate-containing compounds with the nucleophilic compounds. The reaction can be represented by the following equation, R, R', R", R'" and T being as defined above:

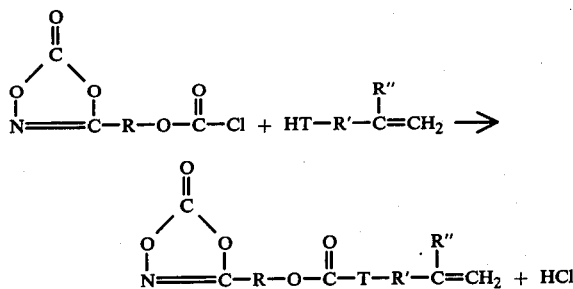

The condensation reaction of the present invention can generally be conducted at a temperature above about −10° C but below that at which the cyclic nitrile carbonate ring reacts with the nucleophilic compound and below the point of decomposition (e.g., to an isocyanate) or the desired addition product, for example, in the range of −10 to 60° C, preferably about 20 to 40 or 50° C. Control of the temperature of the reaction, which is exothermic, can be achieved, for example, by effecting gradual addition of the nucleophilic reactant to the chloroformate, or by contacting the reaction mixture with a cooling medium, or by employing both means.

To insure a fast rate of reaction, it is preferred that the condensation be conducted while the reactants are in contact with a hydrogen chloride acceptor. Generally suitable hydrogen chloride acceptors are basic materials which are non-reactive with the reactants or the addition product but which are effective to neutralize the hydrogen chloride produced. Most preferably the amount of HCl acceptor employed will be at least that which is stoichiometrically required. Inorganic bases, such as the alkali metal hydroxides, carbonates, and bicarbonates, e.g., sodium hydroxide, carbonate, and bicarbonate, as well as organic bases, such as the nitrogenous bases, e.g., pyridine, tertiary amines such as N,N-dimethylaniline, etc., can be used as the HCl acceptor.

Bases, most especially organic bases, often tend to catalyze a reaction between reactive hydrogen-containing groups and cyclic nitrile carbonate groups. Therefore, when a basic HCl acceptor is employed in the present process, it is preferred that essentially no excess of the nucleophilic compound be employed. Thus, at least a stoichiometric amount of the chloroformate is preferably used in that circumstance.

The reaction is preferably carried out with the reactants being homogeneously mixed together, either in the presence or absence of an inert solvent. The presence of a solvent for both reactants is preferred, however. Suitable solvents, include, for example, p-dioxane, chloroform, diethylether, and benzene. Mixtures of solvents, even mutually immiscible solvents such as chloroform and water, or diethylether and water, can also be used if desired. It is preferred that the reaction mixture be agitated during the condensation reaction, especially when a mixture of immiscible solvents is employed, since in this case the condensation often takes place at the solvent interface.

Recovery of the addition product from the reaction mixture can be by any suitable means, such as, for example, by solvent extraction methods. Where a hydrogen chloride acceptor is used, it is generally preferred to neutralize any unreacted amounts thereof which might be present in the crude mixture. This can conveniently be accomplished by washing the mixture with a dilute aqueous solution of an acid such as HCl.

Examples of the novel compounds of the invention are 5-(acryloyloxycarbonyloxypropyl)-1,3,4-dioxazol-2-one, 5-(methacryoyloxycarbonyloxybutyl)-1,3,4-dioxazol-2-one, 5-(3-butenoyloxyethoxycarbonyloxypentyl-1,3,4-dioxazol-2-one, 5-(acrylamidocarbonyloxyhexyl)-1,3,4-dioxazol-2-one, 5(thioacrylyloxycarbonyloxypentyl)-1,3,4-dioxazol-2-one, 5(α-chloroacrylyloxycarbonyloxybutyl)-1,3,4-dioxazol-2-one, 5-[p-(3-butenyloxycarbonyloxy)phenyl]-1,3,4-dioxazol-2-one, 5-(p-butenylphenoxycarbonyloxydecyl)-1,3,4-dioxazol-2-one, 5-(3-butenylaminocarbonyloxybutyl)-1,3,4-dioxazol-2-one, 5-(N-propyl-5-hexenylaminocarbonyl-oxyhexyl)-1,3,4-dioxazol-2-one, 5-(allylmercaptocarbonyloxypentyl)-1,3,4-dioxazol-2-one, the compound having the formula:

$$CH_2=CH-CH-(O-CH_2)_{10}-O-\overset{O}{\underset{\|}{C}}-O-(CH_2)_5-\overset{\overset{O}{\underset{\|}{C}}}{\underset{O\quad O}{|\quad|}}C=N,$$

5-(1,3-butadiene-2yl-methoxycarbonyloxypentyl)-1,3,4-dioxazol-2-one, 5-[(o-allylphenyl)-formyloxypentyl]-1,3,4-dioxazol-2-one, 5-(allylureylenecarbonyloxpentyl)-1,3,4-dioxazol-2-one, etc. As previously noted, compounds of the invention may contain halogen atoms or the above-described non-interfering oxygen, sulfur or nitrogen radicals.

The invention will be better understood by reference to the following examples. Unless stated otherwise, parts and percentages are on a weight basis.

EXAMPLE 1

5-(Choroformyloxypentyl)-1,3,4-dioxazol-2-one, (35.34g, 0.15 moles) is dissolved in 75 ml 1,4-dioxane and cooled to about 10° C. Allyl alcohol (9.59g, 0.165 moles) is added and the solution is warmed to 20 to 22° C. At this temperature and with good stirring 11.86g (0.15 moles) pyridine dissolved in 65 ml 1,4-dioxane is added uniformly over a 1 hour period. Stirring of the reaction mixture is continued at room temperature for another 3 hours. A clear solution is obtained upon addition of 400 ml chloroform. The clear solution is washed 3 times with ice water, dried over Drierite and the solvent evaporated under vacuum. A slightly yellowish liquid obtained (36.8g, 95.4% yield) is identified by IR and NMR spectroscopy to to 5-(allyloxycarbonyloxypentyl)-1,3,4-dioxazol-2-one, having the following structural formula;

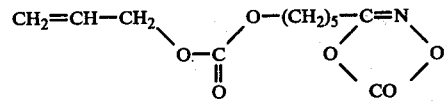

EXAMPLE 2

5-(Chloroformyloxypentyl)-1,3,4-dioxazol-2-one (23.56g = 0.10 mole) is dissolved in 50 ml 1,4-dioxane and cooled to freezing temperature. 2-Hydroxymethyl-1,3-butadiene (8.41g = 0.10 mole) is added, the solution warmed and held at 17 to 20° C while 7.91g (0.10 mole) pyridine dissolved in 50 ml 1,4-dioxane is added uniformly over a 1 hour period with continuous stirring. The reaction mixture is stirred for 3 additional hours at room temperature. The product is dissolved in 300 ml chloroform, washed 3 times with ice water, dried over Drierite and evaporated to dryness. To avoid spontaneous polymerization 0.56 mg (22 ppm)pyrogallol is added to the resulting oil. The product (25.74g = 91.0% yield) is analyzed by IR and NMR spectroscopy and found to be 5-(1,3-butadiene-2-yl-methoxy-carbonyloxypentyl)-1,3,4-dioxazol-2-one, having the following structural formula:

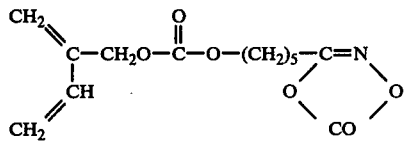

EXAMPLE 3

2-Allylphenol (4.70g = 0.035 moles) and 2.76g (0.035 moles) pyridine dissolved in 11 ml 1,4-dioxane are added over a 1 hour period to a well stirred solution of 8.25g (0.035 moles) 5-(chloroformyloxypentyl)-1,3,4-dioxazol-2-one in 25 ml 1,4-dioxane at 40° C. Stirring is continued at 53° C for 1½ hours. The product is then dissolved in 150 ml chloroform, washed 3 times with ice water, dried over Drierite and evaporated under vacuum. The residue, 11.67g of yellow liquid is analyzed by IR and NMR spectroscopy and found to contain 69.4 wt. % of 5-[(o-allylphenyl)-formyloxypentyl]-1,3,4-dioxazol-2-one (yield = 69.4%), having the following structural formula:

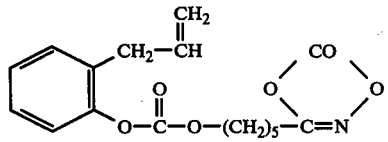

EXAMPLE 4

In accordance with the procedure of Example 1, 35.34g (0.15 moles) 5-(chloroformyloxypentyl)-1,3,4-dioxazol-2-one is reacted with 21.47g (0.165 moles) hydroxyethylmethacrylate in 75 ml 1,4-dioxane by adding 11.86g (0.15 moles) pyridine in 65 ml 1,4-dioxane over a 1 hour period at 19–21° C. After work-up, 47.30g of a slightly brown liquid is obtained which is analyzed by IR and NMR spectroscopy to be 5-[(methacryloyloxyethyl) formyloxypentyl]-1,3,4-dioxazol-2-one (yield 95.7%), having the following formula:

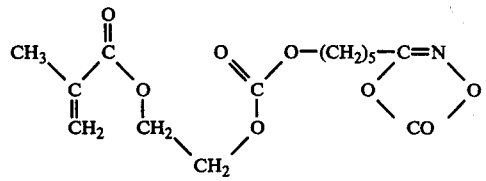

EXAMPLE 5

In accordance with the procedure of Example 1, 35.34g (0.15 moles) 5-(chloroformyloxypentyl)-1,3,4-dioxazol-2-one is made to react with 21.63g (0.15 moles) hydroxypropylmethacrylate (a 1:1 mixture of 2-hydroxypropyl and 1-methyl-2-hydroxyethylmethacrylate) in 75 ml 1,4-dioxane by adding 11.86g (0.15 moles) pyridine in 65 ml 1,4-dioxane over a 1 hour period at 18–21° C. After work-up, 50.0g of a slightly reddish-brown liquid is obtained which is analyzed by IR and NMR spectroscopy to be a 1:1 mixture of 5-[(2-methacryloyloxy-1-methylethyl)formyloxypentyl]-1,3,4-dioxazol-2-one and 5-[(2-methacryloyloxy-2-methylethyl)-formyloxypentyl]-1,3,4-dioxazol-2-one (yield: 97.2%), having the respective structural formulas:

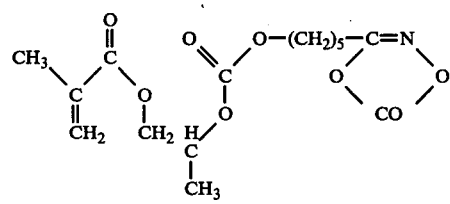

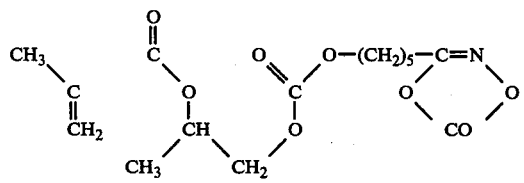

EXAMPLE 6

Allylamine (2.85g = 0.05 moles) and 3.95g (0.05 moles) pyridine dissolved in 20 ml 1,4-dioxane are added over a 1 hour period to a well stirred solution of 11.78g (0.05 moles) 5-(chloroformyloxypentyl)-1,3,4-dioxazol-2-one in 25 ml 1,4-dioxane at 6 to 8° C. Stirring is continued for 3½ hours at room temperature. Chloroform (150 ml) is added to obtain a clear solution which is washed 3 times with ice water, dried over Drierite and evaporated to dryness. The yellow solid (11.48g) obtained is analyzed by IR and NMR spectroscopy to be 5-(allylcarbamoyloxypentyl)-1,3,4-dioxazol-2-one (yield: 89.8%), having the following structural formula:

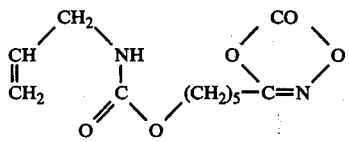

EXAMPLE 7

Allylurea (5.00g = 0.05 moles) and 3.95g (0.05 moles) pyridine dissolved in 20 ml 1,4-dioxane are added over a ¼ hour period to a solution of 11.78g (0.05 moles) 5-(chloroformyloxypentyl)-1,3,4-dioxazol-2-one in 25 ml 1,4-dioxane at 7 to 9° C. Stirring is continued for 3 hours at room temperature, 150 ml chloroform is added, and the mixture is washed 3 times with ice water, dried over Drierite and solvent evaporated under vacuum. A yellowish solid (12.2g) was obtained (MP: 73.0° C, recrystallized from chloroform)which analyzed by IR and NMR spectroscopy to be 5-(allylureylene carbonyloxypentyl)-1,3,4-dioxazol-2-one (yield: 81.6%) having the structural formula:

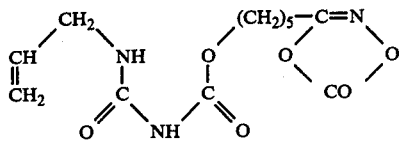

EXAMPLE 8

The procedure of Example 1 is repeated except that acrylic acid is substituted for the allyl alcohol. The product obtained will be 5-(acrylyloxycarbonyloxypentyl)-1,3,4-dioxazol-2-one.

EXAMPLE 9

The procedure of Example 1 is repeated except that the product of the reaction between allyl alcohol and propylene oxide containing an average of 30 carbon atoms is substituted for the allyl alcohol. The resulting compostion will be comprised of compounds containing a terminal ethylenically unsaturated group and a terminal cyclic nitrile carbonate group and which can be polymerized to produce solid polymers useful for potting agents, etc.

EXAMPLE 10

The procedure of Example 1 is repeated except that 5-(p-chloroformyloxyphenyl)-1,3,4-dioxazol-2-one is substituted for the 5-(chloroformyloxypentyl)-1,3,4-dioxazol-2-one. The product obtained will be 5-(p-allyloxycarbonyloxyphenyl)-1,3,4-dioxazol-2-one.

EXAMPLE 11

The procedure of Example 1 is repeated except that 4,5-epoxy-1-pentene is substituted for the allyl alcohol. The product will be 5-(1-pentenyloxycarbonyloxypentyl)-1,3,4-dioxazol-2-one.

EXAMPLE 12

A mixture of 5.170g (20.1 mmoles) 5-(allyloxycarbonyloxypentyl)-1,3,4-dioxazol-2-one (prepared in Example 1) 0.733g (7.0 mmoles) styrene and 0.177g (3%) benzoylperoxide is placed in an ampoule, flushed with nitrogen, sealed and submerged in a stirred oil bath at 80° C for 47 hours. The reaction product is poured into 100 ml of ethyl ether. An oil is separated, dissolved in 10 ml benzene and reprecipitated in 100 ml of ethyl ether. After separation of the two phases and complete evaporation of the solvent under vacuum 1.04g of viscous oil remained which is determined by IR and NMR spectroscopy to be a copolymer of the allyl derivative with styrene in a 4:1 ratio. The polymer yield is 17.6%.

EXAMPLE 13

A mixture of 0.9g (3.2 mmoles) 5-(1,3-butadiene-2-yl-methoxycarbonyloxypentyl)-1,3,4-dioxazol-2-one, (prepared in Example 2) 8.1g (78 mmoles) styrene and 0.18g (2%) AIBN is placed in an ampoule, flushed with nitrogen, sealed and submerged in a stirred oil bath at 50° C for 24 hours. A glass clear, hard solid is obtained which shows swelling but little, if any, solubility in most common solvents indicating at least some degree of crosslinking. A sample is dissolved in n-decylchloride at 120 to 130° C and inspected by IR spectroscopy. Polystyrene bands are clearly visible but also are those characteristic bands of 1,3,4-dioxazol-2-ones.

EXAMPLE 14

5-[(Methacryloyloxyethyl)formyloxypentyl]-1,3,4-dioxazol-2-(prepared in Example 4), 2.305g (7 mmoles), 7.290g (70 mmoles) styrene and 0.2g (2.1%) benzoylperoxide are dissolved in 50 ml dried methylisobutylketone and stirred at 90° C for 6 hours. The resulting solution is slowly added to 500 ml 1:1 pentane/ether under continuous stirring. The resulting oil is decanted, dissolved in 80g benzene and freeze-dried to give 2.15g of a white, fluffy and readily soluble powder. The product is analyzed by IR and NMR spectroscopy and found to be the desired copolymer. GPC analysis gives the following results: $\overline{M}w = 11,300$, $\overline{M}n = 7,800$ (Q value = 41), $\overline{A}w/\overline{A}n = 1.44$.

EXAMPLE 15

5-[(Methacryloyloxyethyl)formyloxypentyl]-1,3,4-dioxazol-2-one (prepared in Example 4), 2.305g (7 mmoles), 7.22g (70 mmoles) methylmethacrylate and 0.1g (1%) benzoylperoxide are dissolved in 50 ml methylisobutylketone and heated to 90° C. After 7 hours an additional 0.1g (1%) benzoylperoxide is added and the mixture is heated and stirred for a total of 24 hours. The solution is then slowly poured into 6000 ml 1:1 pentane/ether under good stirring and the resulting oil freeze-dried from 80g benzene. 7.5g of a white, fluffy soluble solid is obtained which is analyzed by IR and NMR spectroscopy to be the desired copolymer. GPC analysis results are: $\overline{M}w = 13,900$, $\overline{M}n = 5270$ (Q value = 25), $\overline{A}w/\overline{A}n = 2.65$.

EXAMPLE 16

5-(1,3-Butadiene-2-yl-methoxycarbonyloxypentyl)-1,3,4-dioxazol-2-one (prepared in Example 2) 1.983g (7 mmoles), 7.22g (70 mmoles) methylmethacrylate and 0.1g (1%) benzoylperoxide are dissolved in 50 ml methylisobutylketone and heated to 90° C with stirring. After 7 hours an additional 0.1g (1%) benzoylperoxide is added and heating continued for a total of 24 hours. The solution is then worked-up to give 2.96g of white, fluffy solid which is analyzed by IR and NMR spectroscopy to be the desired copolymer. GPC analysis results are: $\overline{M}w = 4050$, $\overline{M}n = 2630$ (Q value = 25), $\overline{A}w/\overline{A}n = 1.54$.

Examples 1 – 11 illustrate the preparation of representative novel compounds of the invention and Examples 12 – 16 illustrate the use of some of the novel compounds of the invention in the preparation of polymers. The compounds of the invention can be used to prepare solid or liquid polymeric materials having widely varying physical properties. For example, the cmpounds of the invention are useful for the preparation of polymers such as crosslinkable foams, elastomers, drying oils, etc. The polymeric materials are useful for the manufacture of foam insulation, coatings, adhesives, plasticizers, sealants, potting agents, paints, etc.

Although the invention has been described with particular reference to specific examples, it is understood that the scope of the invention is limited only by the breadth of the appended claims.

We claim:

1. A compound having the structural formula:

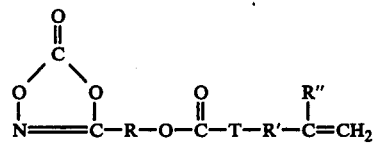

wherein T is O, S, or NR''', R is a substituted or unsubstituted alkylene of 1 to 20 carbon atoms, or a phenylene, R' is a substituted or unsubstituted alkylene of 1 to 12 carbon atoms, carbonyl or phenylene, R" is hydrogen, halogen or a substituted or unsubstituted alkyl or alkylene of 1 to 8 carbon atoms and R''' is hydrogen, or a substituted or unsubstituted alkyl of 1 to 8 carbon atoms, wherein the substituents are compatible members of the group consisting of halo, amido, amino, urea, thiourea, nitro, nitrile, $C_3$-$C_{12}$ ester, $C_3$-$C_{12}$ ether, $C_3$-$C_{12}$ ketone, $C_3$-$C_{12}$ thioester, $C_3$-$C_{12}$ thioether, and $C_3$-$C_{12}$ thioketone.

2. A compound of claim 1 wherein R has 3 to 6 carbon atoms.
3. A compound of claim 1 wherein R' is a carbonyl group.
4. A compound of claim 1 wherein R' is polyoxyethylene substituted.
5. A compound of claim 1 wherein R" is H.
6. A compound of claim 1 wherein R" is an alkyl having up to 8 carbon atoms.
7. A compound of claim 1 wherein R" is a vinyl group.
8. A compound of claim 1 wherein R" is halogen.
9. A compound of claim 1 wherein T is O.
10. A compound of claim 1 wherein R''' is H.
11. A compound of claim 1 wherein R''' is a alkyl of up to 8 carbon atoms.
12. A compound of claim 1 wherein R is an alkyl having 3 to 12 carbon atoms, R' has 1 to 12 carbon atoms, R" is H or methyl, and T is O or NH.
13. A compound of claim 12 wherein R' is carboxyl ester substituted.
14. A compound of claim 12 wherein R' is ether substituted.
15. A compound having the structural formula:

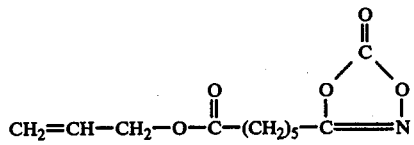

16. The compound having the structural formula:

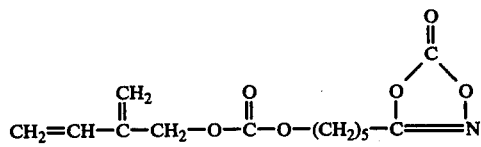

17. The compound having the structural formula:

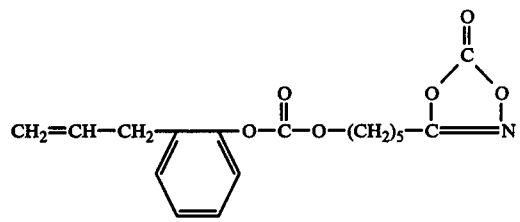

18. The compound having the structural formula:

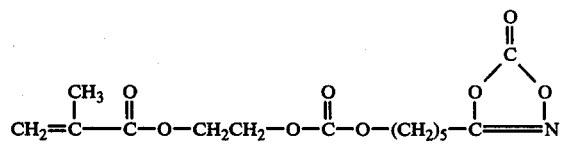

19. The compound having the structural formula:

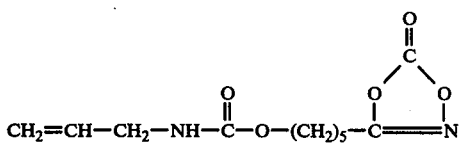

20. The compound having the structural formula:

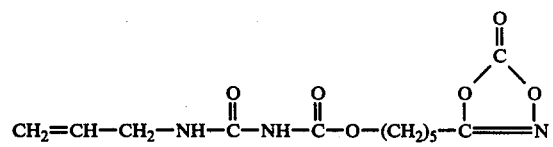

21. Compounds having the structural formula:

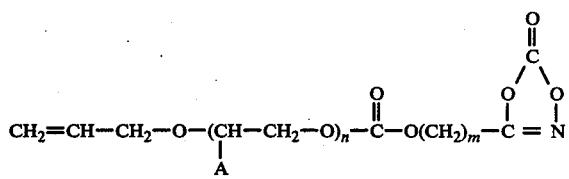

wherein A is hydrogen or $CH_3$, n varies from 1 to 25 and m varies from 3 to 20.

22. Compounds having the structural formula:

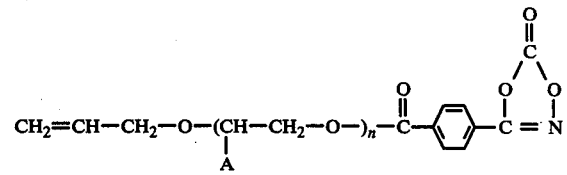

wherein A is hydrogen or $CH_3$, and n varies from 1 to 25.

* * * * *